(12) United States Patent
Rennich et al.

(10) Patent No.: US 11,331,504 B2
(45) Date of Patent: May 17, 2022

(54) BIPOLAR BONE ANCHOR WITH CONNECTION FOR ELECTROSTIMULATION

(71) Applicant: Neue Magnetodyn GmbH, Putzbrunn (DE)

(72) Inventors: Markus Rennich, Munich (DE); Heribert Stephan, Munich (DE)

(73) Assignee: NEUE MAGNETODYN GMBH, Putzbrunn (DE)

( * ) Notice: Subject to any disclaimer, the term of this patent is extended or adjusted under 35 U.S.C. 154(b) by 0 days.

(21) Appl. No.: 16/378,704

(22) Filed: Apr. 9, 2019

(65) Prior Publication Data
US 2019/0308014 A1    Oct. 10, 2019

Related U.S. Application Data

(60) Provisional application No. 62/655,272, filed on Apr. 10, 2018.

(51) Int. Cl.
*A61N 1/378* (2006.01)
*A61N 1/32* (2006.01)
(Continued)

(52) U.S. Cl.
CPC ........... *A61N 1/3787* (2013.01); *A61N 1/326* (2013.01); *A61B 17/58* (2013.01);
(Continued)

(58) Field of Classification Search
CPC ...... A61N 1/3787; A61N 1/326; A61N 1/205; A61N 1/05; A61B 2017/564; A61B 17/58;
(Continued)

(56) References Cited

U.S. PATENT DOCUMENTS

| 3,964,473 A | 6/1976 | Wickham et al. |
| 4,027,392 A | 6/1977 | Sawyer et al. |

(Continued)

FOREIGN PATENT DOCUMENTS

| DE | 102006032957 A1 | 11/2007 |
| EP | 0659098 B1 | 12/1996 |

(Continued)

*Primary Examiner* — Carl H Layno
*Assistant Examiner* — Anh-Khoa N Dinh
(74) *Attorney, Agent, or Firm* — Hassan Abbas Shakir; Shakir Law PLLC

(57) ABSTRACT

An electrical stimulation anchor is configured to be electrically coupled to a power source, such as a transducer, that is external to the electrical stimulation anchor. The electrical stimulation anchor can include a bone anchor that is configured to be secured to a bone. The bone anchor can define a first electrode, a second electrode, and an isolating portion between the first electrode and the second electrode. The electrical stimulation anchor can further include a connection unit attached to the bone anchor. The connection unit can define a first contact member that electrically connects to the first electrode, and a second contact member electrically isolated from the first contact member. The second contact member can be electrically connected to the second electrode. The first and second contact members are configured to draw electrical current from the transducer so as to establish a voltage differential between the first and second electrodes.

17 Claims, 12 Drawing Sheets

(51) Int. Cl.
*A61N 1/05* (2006.01)
*A61B 17/86* (2006.01)
*A61B 17/56* (2006.01)
*A61B 17/58* (2006.01)
*A61N 1/20* (2006.01)

(52) U.S. Cl.
CPC .......... *A61B 2017/564* (2013.01); *A61N 1/05* (2013.01); *A61N 1/205* (2013.01)

(58) Field of Classification Search
CPC ... A61B 17/72; A61B 17/8605; A61B 17/863; A61B 17/8635; A61B 17/866; A61B 17/8685
See application file for complete search history.

(56) References Cited

U.S. PATENT DOCUMENTS

| | | | |
|---|---|---|---|
| 5,292,252 | A | 3/1994 | Nickerson et al. |
| 6,034,295 | A | 3/2000 | Rehberg et al. |
| 6,778,861 | B1 | 8/2004 | Liebrecht et al. |
| 8,425,395 | B2 | 4/2013 | Kraus et al. |
| 2007/0265682 | A1* | 11/2007 | Wiegmann ............. A61N 1/326 607/51 |
| 2008/0255556 | A1* | 10/2008 | Berger ............... A61B 17/8685 606/60 |
| 2009/0054951 | A1* | 2/2009 | Leuthardt .......... A61B 17/8625 607/46 |
| 2009/0143781 | A1 | 6/2009 | Mische |
| 2010/0298886 | A1* | 11/2010 | Kraus ................ A61B 17/8685 606/301 |
| 2012/0276501 | A1* | 11/2012 | Terkel ................... A61F 2/3662 433/173 |
| 2012/0277812 | A1* | 11/2012 | Kraus .................... A61B 17/86 606/86 R |

FOREIGN PATENT DOCUMENTS

| | | |
|---|---|---|
| EP | 1847227 A1 | 10/2007 |
| EP | 2050482 A1 | 4/2009 |
| EP | 2361589 A1 | 8/2011 |
| EP | 2467190 B1 | 3/2014 |
| WO | 97/36551 A1 | 10/1997 |
| WO | 2007/124731 A2 | 11/2007 |
| WO | 2007/131560 A1 | 11/2007 |
| WO | 2008/127592 A1 | 10/2008 |
| WO | 2009/083086 A2 | 7/2009 |

* cited by examiner

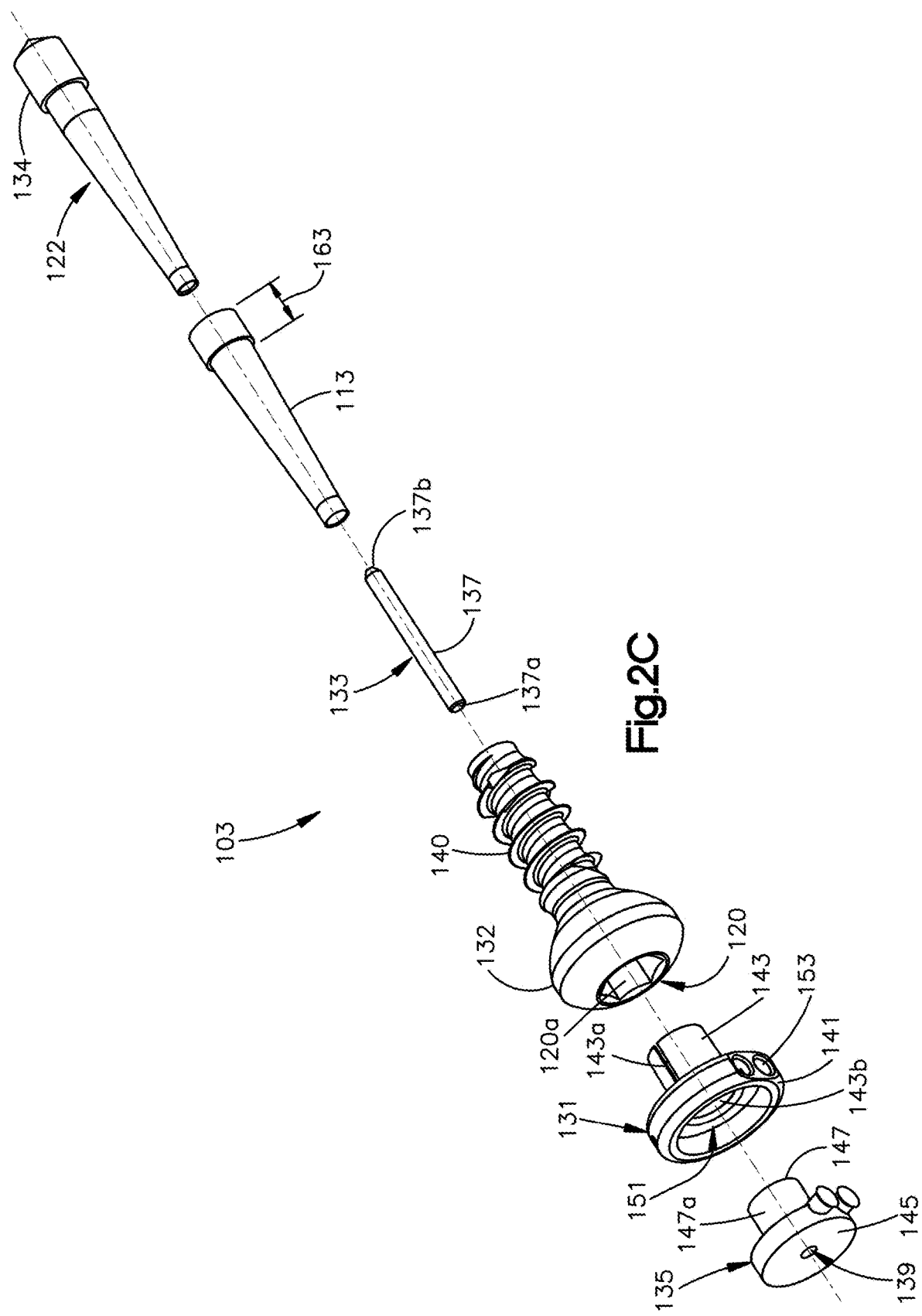

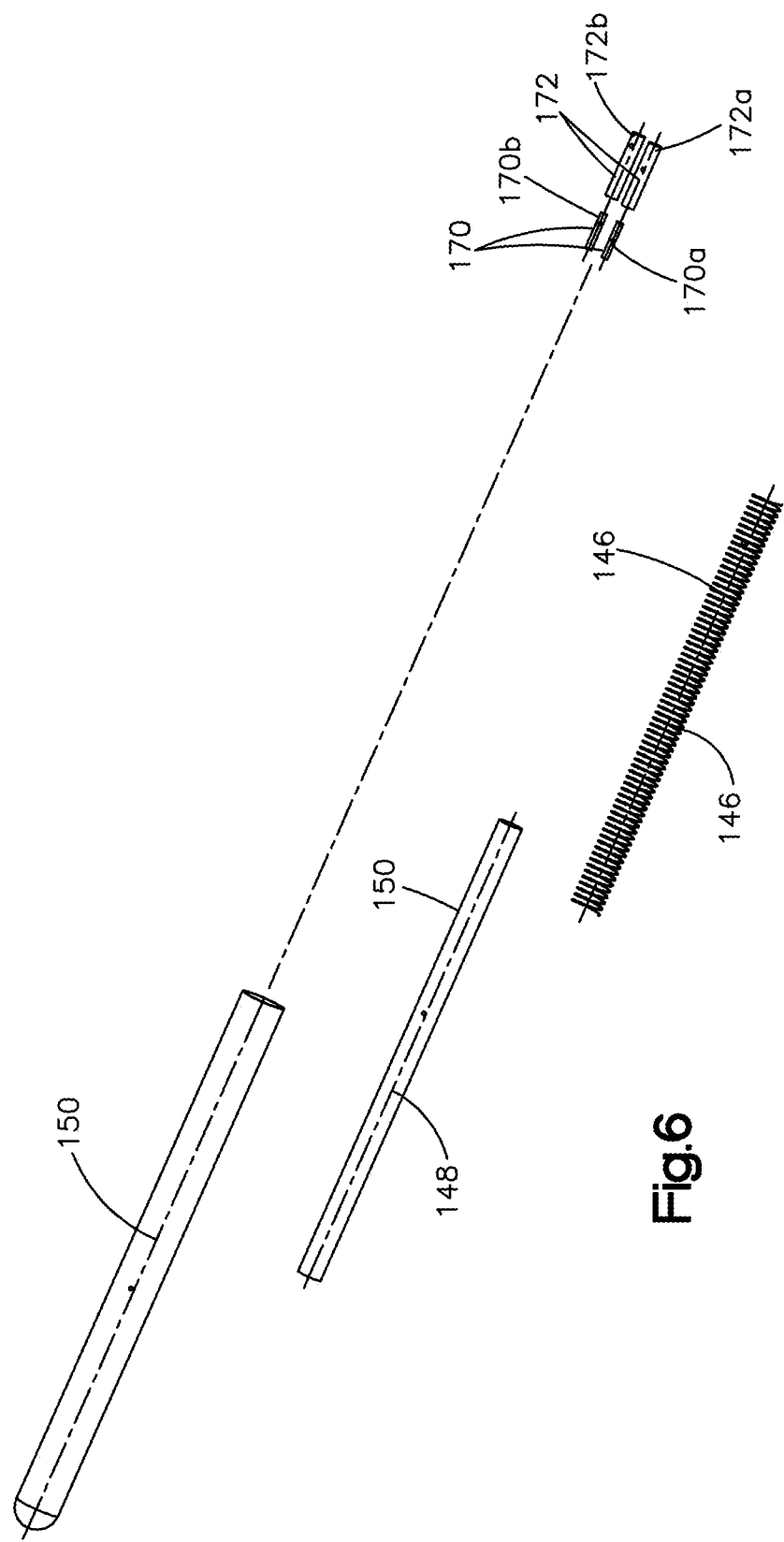

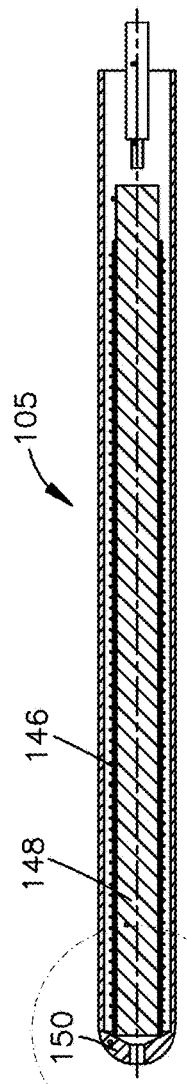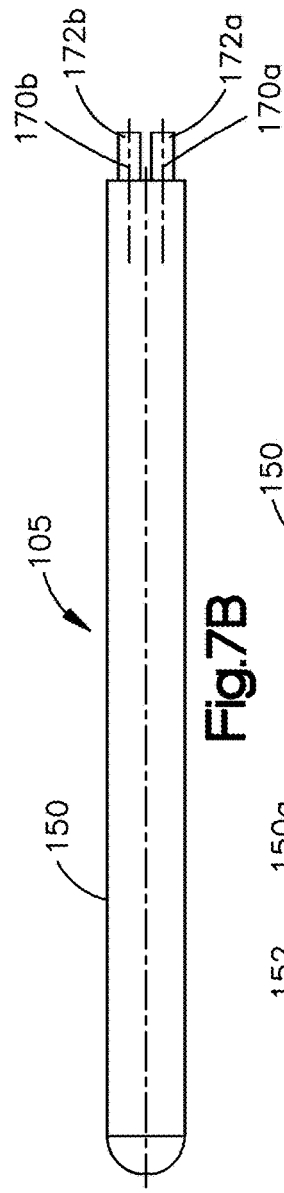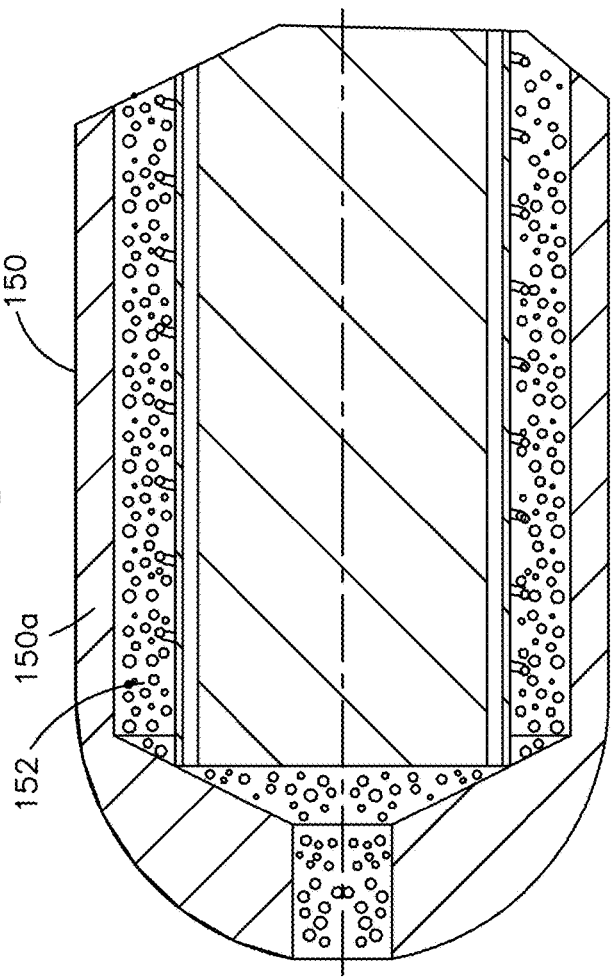

BIPOLAR BONE ANCHOR WITH CONNECTION FOR ELECTROSTIMULATION

CROSS REFERENCE TO RELATED APPLICATIONS

This application claims benefit under 35 U.S.C. § 119(e) of Provisional U.S. Patent Application No. 62/655,272, filed Apr. 10, 2018, the contents of which are hereby incorporated by reference in its entirety.

TECHNICAL FIELD

This disclosure relates generally to bone fixation implants, and in particular relates to implants that can perform electromagnetic stimulation of a bone fracture to improve healing of the bone fracture.

BACKGROUND

When bones are damaged through trauma, disease, distraction osteogenesis, or orthognathic surgery, bone fixation implants are commonly used to provide anatomical re-alignment of bone fragments, to maintain their position, and to ensure union in the desired position. Thus, bone fixation implants are typically designed to achieve proper anatomic fit and function. Additionally, because bone fixation implants often support bones that withstand significant mechanical stress in their anatomic function, implants are often composed of strong and rigid materials.

Bone anchors can be configured to electrically stimulate bone fracture repair or to counteract infection when the bone anchors are exposed to an external electromagnetic field. Such bone anchors can include coils of wire, or transformers, which induce an electrical field. Bone anchors that include transformers are sized so as to generate an electrical field that has sufficient strength to stimulate healing of the bone fracture or counteraction of the infection. In some cases, a bipolar bone screw for a stand-alone application is required to generate an electric field of about 700 mV when induced with an external alternating magnetic field of about 5 mT. It is recognized herein that, in some cases, bone anchors configured for electrical stimulation of this power may be limited by current technology to be no shorter than about 70 mm in length, and to have a core diameter no less than about 5 mm.

SUMMARY

In an example aspect, an electrical stimulation anchor is configured to be electrically coupled to a power source, such as a transducer, which is external to the electrical stimulation anchor. The electrical stimulation anchor can include a bone anchor that is configured to be secured to a bone. The electrical stimulation anchor can further include a connection unit attached to the bone anchor. The bone anchor can include a first electrode, a second electrode, and an isolating or insulative portion between the first electrode and the second electrode. The connection unit can include a connection unit insulator configured to electrically isolate the first electrode with respect to the second electrode when the power source is electrically connected to the first and second electrodes, so as to establish a voltage differential between the first and second electrodes. The connection unit can further include a first contact member that electrically connects to the first electrode, and a second contact member electrically isolated from the first contact member. The second contact member can be electrically connected to the second electrode. The first and second contact members can be configured to draw electrical current from the transducer so as to establish the voltage differential between the first and second electrodes. For example, the connection unit can be further configured to electrically connect to a first contact of the power source having a first polarity, and a second contact of the power source having a second polarity opposite the first polarity.

In another example, a fracture in a bone is treated by positioning an electrical stimulation anchor in the bone such that the fracture is disposed adjacent to first and second electrodes of the electrical stimulation anchor. The method of treating the fracture includes inserting a bone anchor defining the first and second electrodes into the bone. The method of treating the fracture further includes electrically connecting the first and second electrodes, via first and second contact members of the electrical stimulation anchor, to a transducer that is external to the electrical stimulation anchor. The transducer can be exposed to an alternating magnetic field, so as to generate a current in an electrical coil of the transducer. The electrical current is transferred to the first and second contact members, and thus to the first and second electrodes that are electrically connected to the first and second contact members, so as establish a voltage differential between the first and second electrodes.

The foregoing summarizes only an example of the present disclosure and associated technology and is not intended to be reflective of the full scope of the present disclosure. Additional features and advantages of the disclosure are set forth in the following description, may be apparent from the description, or may be learned by practicing the invention. Moreover, both the foregoing summary and following detailed description are explanatory examples intended to provide further explanation of the disclosure.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings:

FIG. 2C is an exploded view of the electrical stimulation anchor depicted in FIGS. 2A and 2B.

FIG. 6 is an exploded view of an example transducer of the electrical stimulation anchor system shown in FIG. 1.

FIG. 7A is a cross section of the transducer shown in FIG. 6.

FIG. 7B is a side elevation view of the transducer shown in FIG. 7A.

FIG. 7C is a cross section of a portion of the transducer depicted in FIGS. 7A and 7B.

DETAILED DESCRIPTION

As an initial matter, aspects of the disclosure will now be described in detail with reference to the drawings, wherein like reference numbers refer to like elements throughout, unless specified otherwise. Certain terminology is used in the following description for convenience only, and is not limiting. The term "plurality", as used herein, means more than one. The terms "a portion" and "at least a portion" of a structure include the entirety of the structure. Certain features of the disclosure that are described herein in the context of separate embodiments may also be provided in combination in a single embodiment. Conversely, various features of the disclosure that are described in the context of a single embodiment may also be provided separately or in any sub-combination.

Figure 1:
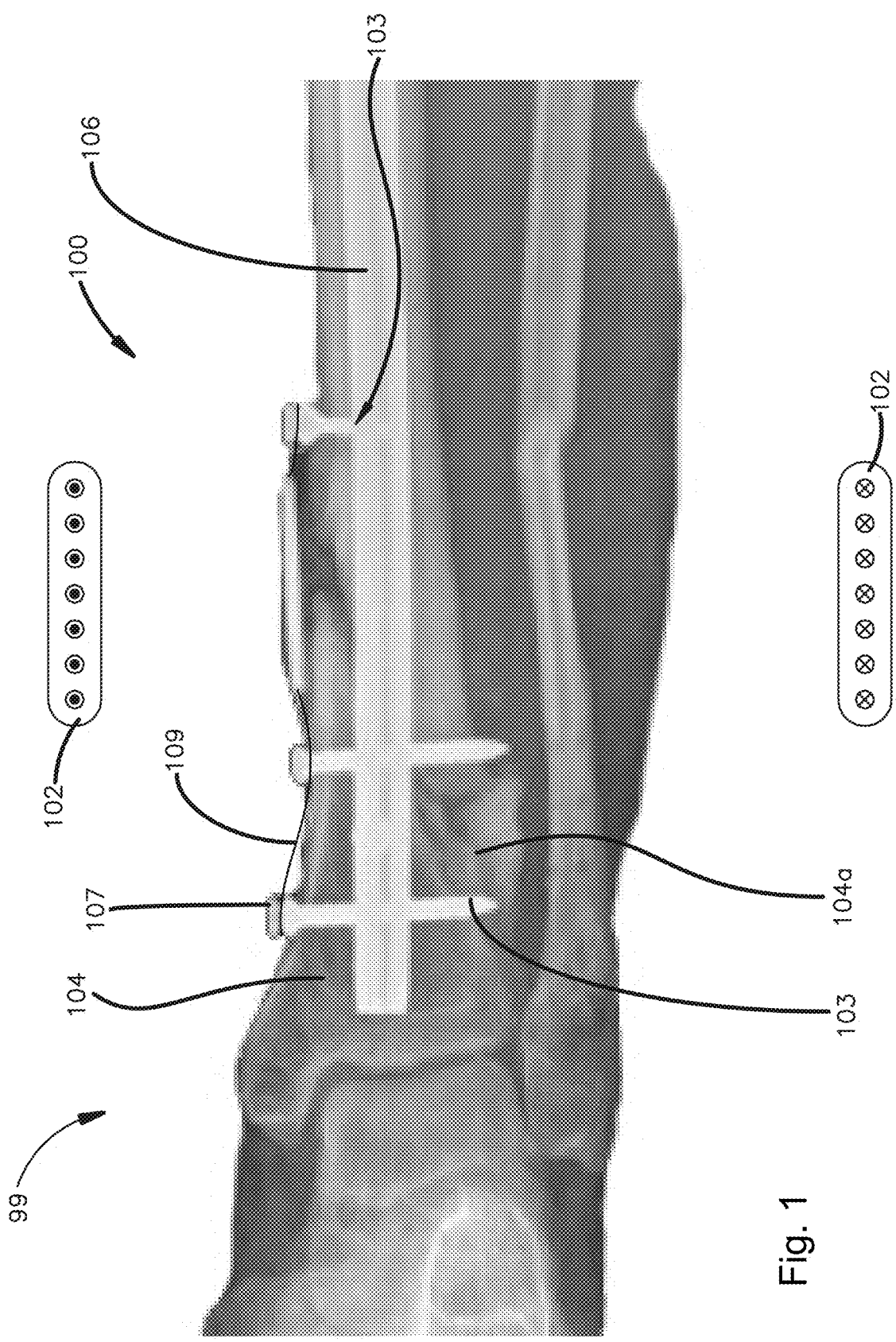
FIG. 1 depicts an electrical stimulation anchor system in accordance with an example embodiment, wherein the electrical stimulation anchor system includes bone anchors that secure an implant to a bone.

Referring to FIG. 1, an electrical stimulation system 99 can include an electrical stimulation anchor system 100, a pulsed electromagnetic field (PEMF) device 102, and a bone implant 106. The bone implant 106 can be configured to be implanted and secured to a bone 104 so as to treat a fractured portion 104a of the bone 104. It will be appreciated that the bone 104 can be any bone in the human or animal anatomy suitable for bone implants. Further, it will be understood that the bone 104 can define any number of fractured portions or bone segments as desired that are configured for fixation using the electrical stimulation system 99.

The electrical stimulation system 99 can include the implant 106, for instance a bone plate or nail, and the electrical stimulation anchor system 100 that can secure the implant 106 to the underlying bone, or alternatively can be secured to the bone 104 without the implant 106. The electrical stimulation anchor system 100 can include at least one electrical stimulation anchor 103 and at least one power source, such as a transducer or transformer 105, which is external to the electrical stimulation anchor 103. For purposes of example, the power source is referred to herein as a transducer or transformer, though it will be understood that the electrical stimulation anchor can be coupled to alternative power sources as desired. For example, the power source can include various in-body energy sources, such as a bio-compatible internal energy source that includes a power capacitor, battery, or other energy harvesting or storage devices. Thus, the power source may be a self-supply or self-contained generator having an energy storage component, such as accumulator or battery for example. The power source may also include a bio-compatible device with an additional electrical coil (e.g., with or without a soft magnetic core), which makes it possible to charge the integrated energy source (e.g., accumulator, battery, supercapacitor) by inductive coupling of external alternating magnetic fields Referring to FIG. 1, the electrical stimulation anchor 103 can be configured to electrically connect any power source, such as the transducer 105. As used herein, unless otherwise specified, the transducer 105 can also be referred to as a transformer 105, without limitation. The electrical stimulation anchor 103 can include a bone anchor 108 that is configured to secure the implant 106 to the underlying bone 104. Alternatively, in accordance with another example, the bone anchor 108 can be configured to purchase in the bone 104 without the implant 106. The bone anchors 108 can be alternatively configured as bone pins. For purposes of example, bones screws are described herein, though it will be understood that the bone anchors 108 can be alternatively configured so as to insert into the bone 104, and all such alternatives are contemplated as being within the scope of this disclosure.

Referring to FIGS. 2A to 2D, the electrical stimulation anchor 103 can further include a connection unit 107 attached to the bone anchor 108. The electrical stimulation anchor system 100 can further include at least one electrically conductive member, for instance at least one wire 109 that electrically couples the electrical stimulation anchor with the transducer 105. In an example, the wire 109 includes multifiliar pacemaker wires, though it will be understood that the wire 109 may be alternatively composed as desired, so as to transfer electrical current between the connection unit 107 and the transducer 105. For example, the wire 109 can include one or more electrical conductors. In particular, the connection unit 107 can be configured to electrically connect to the transducer 105 via the wire 109, such that the connection unit 107 can draw electrical current from the transducer 105 over the wire 109. For example, the connection unit 107 can be further configured to electrically connect to a first contact of the power source having a first polarity, and a second contact of the power source having a second polarity opposite the first polarity.

Figure 3A:
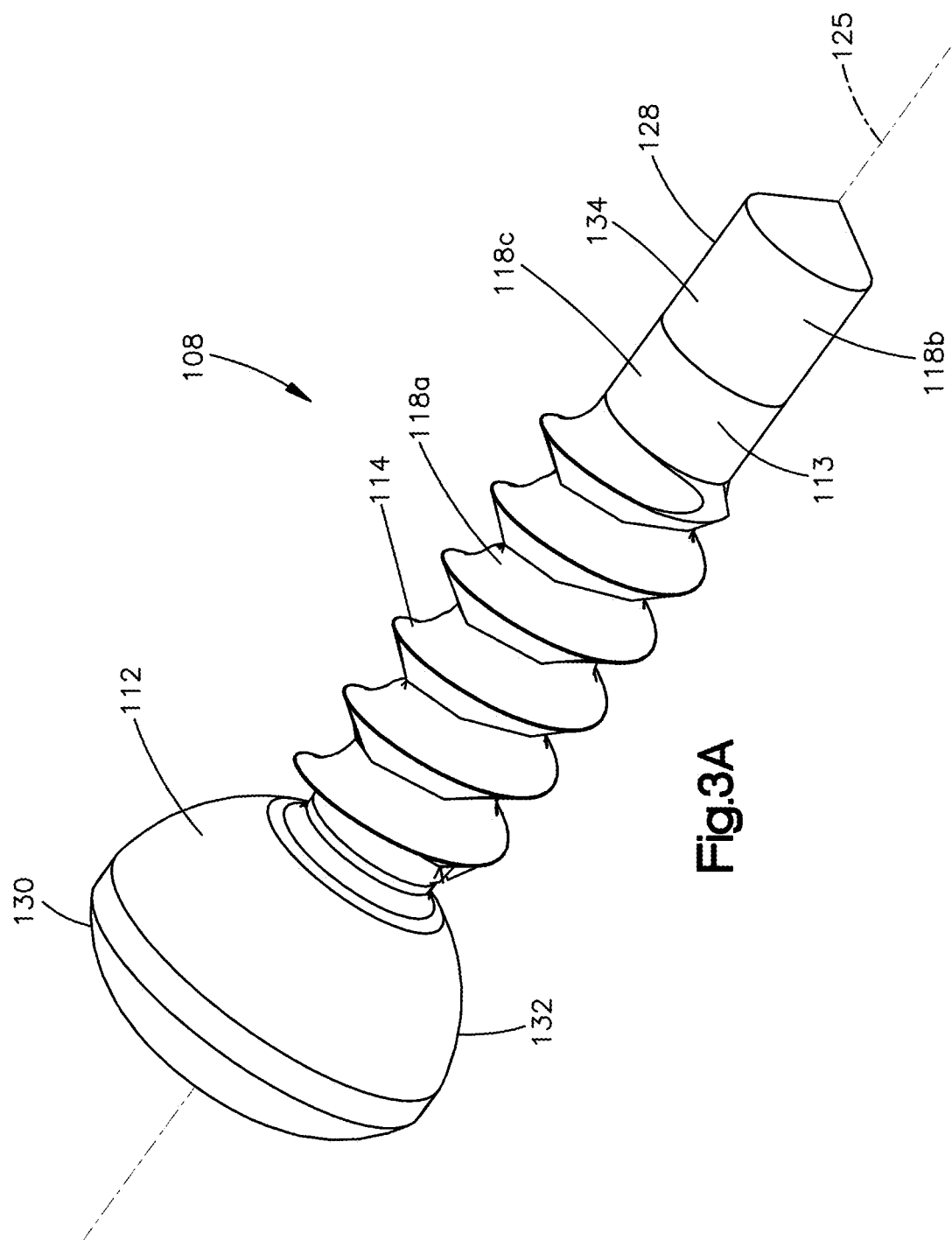
FIG. 3A is a perspective view of the bone anchor shown in FIGS. 2A-D, in accordance with an example embodiment.
Figure 3B:
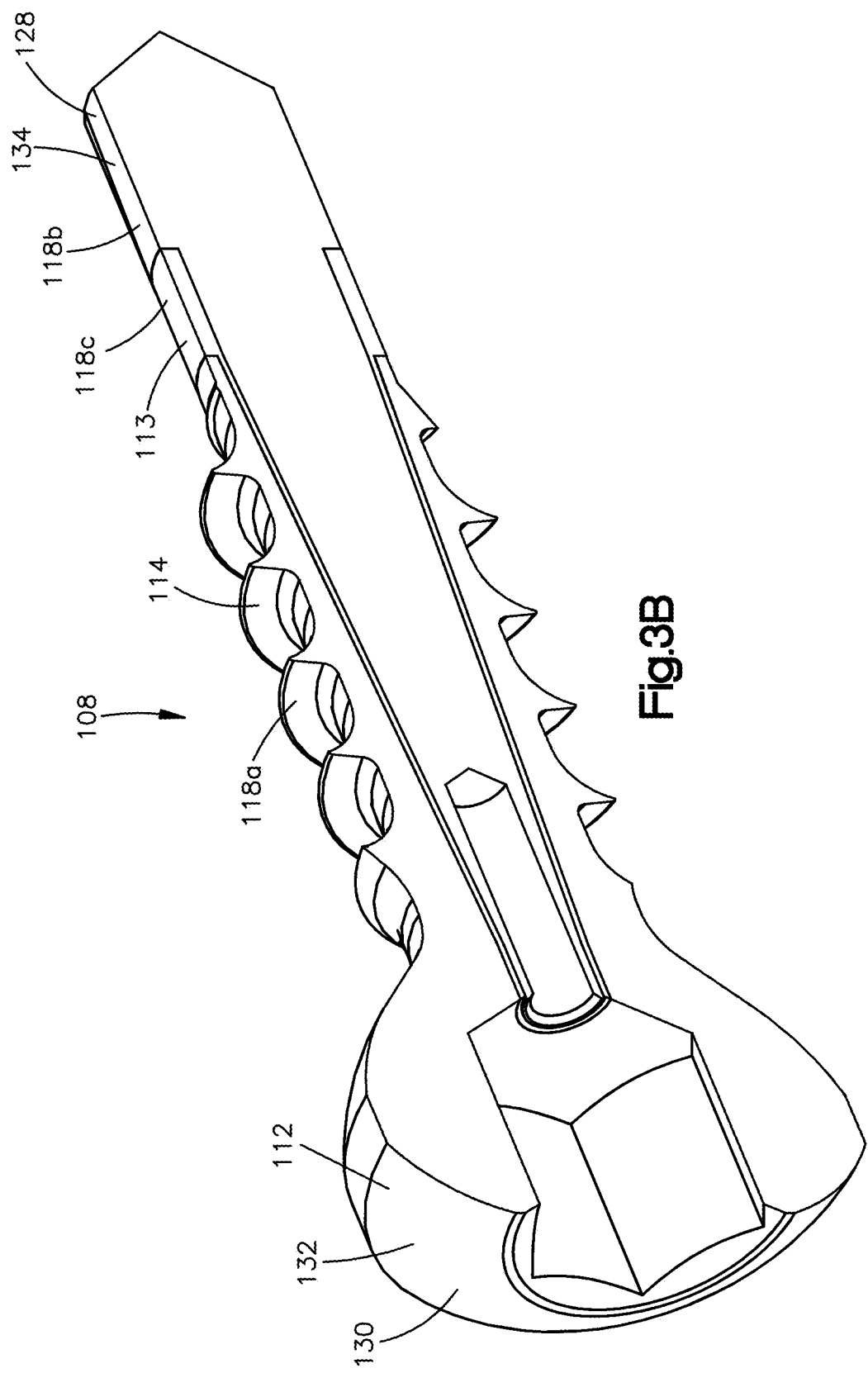
FIG. 3B is a cross section of the bone anchor depicted in FIG. 3A.
Figure 3C:
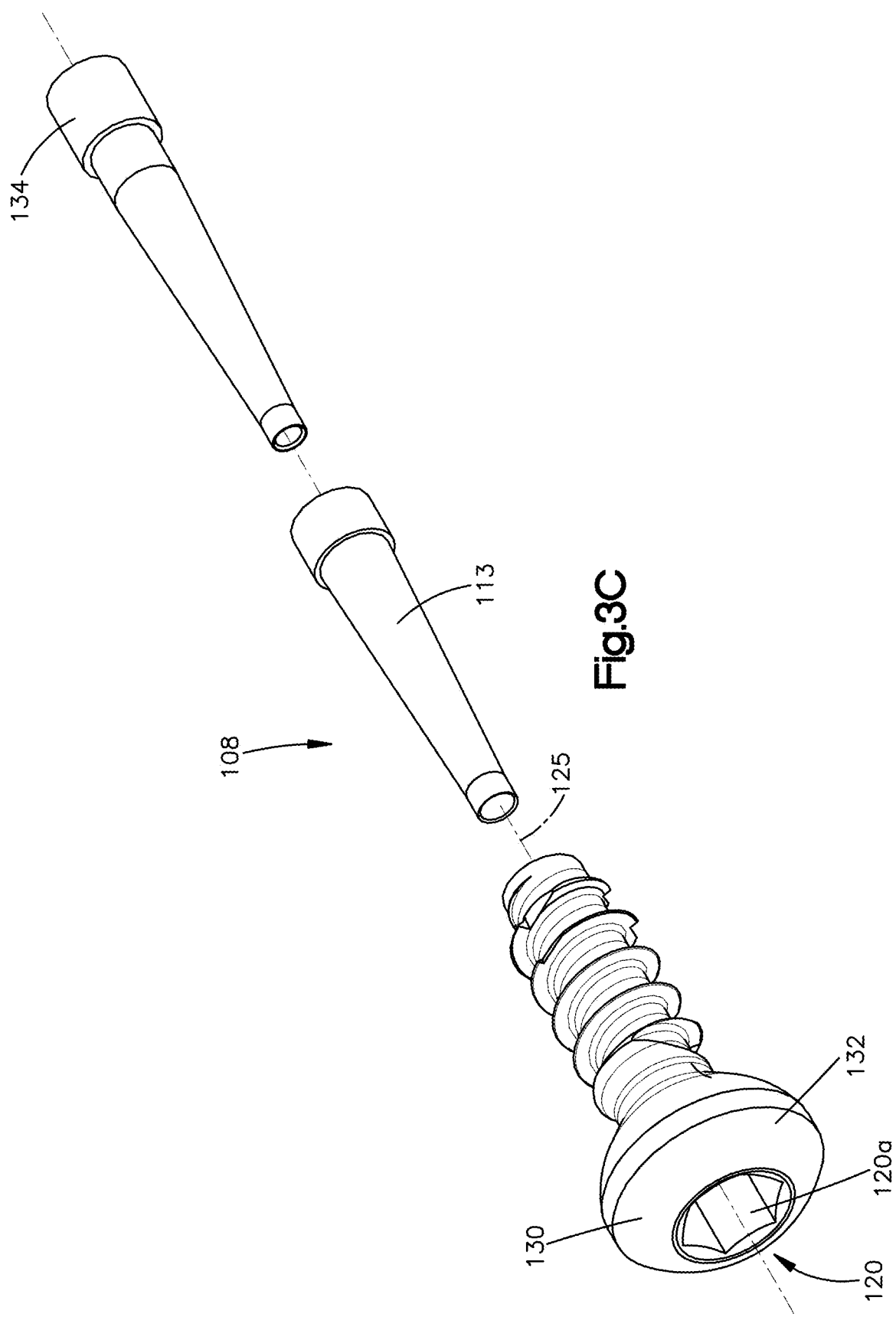
FIG. 3C is an exploded view of the bone anchor shown in FIGS. 3A and 3B.

Referring also to FIGS. 3A to 3C, the bone anchors 108 can include a head 112 and a shaft 114 that extends out with respect to the head 112 along a central anchor axis 125. The shaft 114 can extend directly from the head 112, or can extend from a neck that is disposed between the head 112 and the shaft 114. The shaft 114 can be threaded entirely or in part. Thus, the bone anchor 108 can be configured as a bone screw. The threaded shaft 114 can be configured to threadedly purchase in the underlying bone 104. For instance, the bone anchor 108 can be configured as a cortical screw whose threaded shaft 114 is designed and configured to threadedly mate to cortical bone. Alternatively or additionally, the bone anchor 108 can be configured as a cancellous screw whose threaded shaft 114 is designed and configured to threadedly mate to cancellous bone. It is appreciated that cancellous bone anchors have threads that have a greater pitch than threads of cortical bone anchors. Further, the threads of cancellous bone anchors typically extend out from the shaft 114 of the bone anchor 108 a greater radial distance than the threads of cortical bone anchors. The shaft 114 of the bone anchor 108 can be threaded so as to define a thread that is not continuous from one end of the shaft 114 to the other end of the shaft 114. Alternatively, the shaft 114 can define a thread that is continuous over at least a portion of the shaft, for instance all of the shaft from one end of the shaft 114 to the other end of the shaft 114.

The electrical stimulation anchor system 100 can include one or more electrical stimulation anchors 103. One or more up to all of the bone anchors 108 can be configured as compression screws whose head 112 is configured to bear against the implant 106 so as to apply a compressive force against the implant 106 toward the underlying bone 104 when the shaft 114 is driven further into the underlying bone 104 after the head 112 has contacted the implant 106. The shaft 114 can be driven into the underlying bone a sufficient distance until the desired compressive force has been imparted onto the implant 106. The head 112 of the compression screw can be unthreaded.

In another example, one or more up to all of the bone anchors 108 can be configured as locking screws that are configured to lock to the implant 106. In particular, the head 112 can be externally threaded. In particular, when the bone anchor 108 is a locking screw, rotation of the bone anchor 108 causes the threaded head 112 to threadedly mate with an internal surface of the implant 106. As a result, the screw head 112 fastens the implant 106 to the underlying bone 104 without applying a compressive force onto the implant 106 against the underlying bone 104. The implant 106 can be spaced from the underlying bone 104 when locked to the head 112. Alternatively, the implant 106 can abut the underlying bone 104 when locked to the head 112. The head 112 can define at least one external thread that is circumferentially continuous about the central anchor axis 115. It should be appreciated, however, that the head 112 can be alternatively constructed in any manner desired so as to threadedly mate with the internal surface as described herein.

Referring now to FIGS. 3A-6, the bone anchors 108 can each define a distal end 128 and a proximal end 130 that is opposite the distal end 128, such that the bone anchor 108 is elongate from the proximal end 130 to the distal end 128. The head 112 can be located at the proximal end 130, and the connection unit 107 of the electrical stimulation anchor 103 can be disposed adjacent to, or attached to, the proximal end 130 of the bone anchor 108. The head 112, and thus the proximal end 130, can define a first electrode 132 of the bone anchor 108, and thus the electrical stimulation anchor 103. The distal end 128 can be considered to be an insertion end or leading end, and can define a second electrode 134 of the bone anchor 108, and thus of the electrical stimulation anchor 103. The first and second electrodes 132 and 134 can be spaced from each other so as to be configured to electrically stimulate a fractured portion of the bone 104 adjacent to the first and second electrodes 132 and 134. For example, the first and second electrodes 132 and 134 can be spaced from each other along the central anchor axis 125 so as to be configured to electrically stimulate a fractured portion of the bone 104 between the first and second electrodes 132 and 134 along the central anchor axis 125. The shaft 114 can extend between the proximal end 130 and the distal end 128 along the central anchor axis 125. The shaft 114 can define the threaded portion that can be adjacent to the proximal end 130 and the distal end 128. The bone anchor 108 can further include a tip 136 that is disposed at the distal end 128. The proximal end 130 and the distal end 128 can define opposite outermost ends of the bone anchor 108. The first and second electrodes 132 and 134 can be composed of electrically conductive material, for instance titanium, stainless steel, or alloys thereof, so as to transfer electrical current.

Figure 2A:
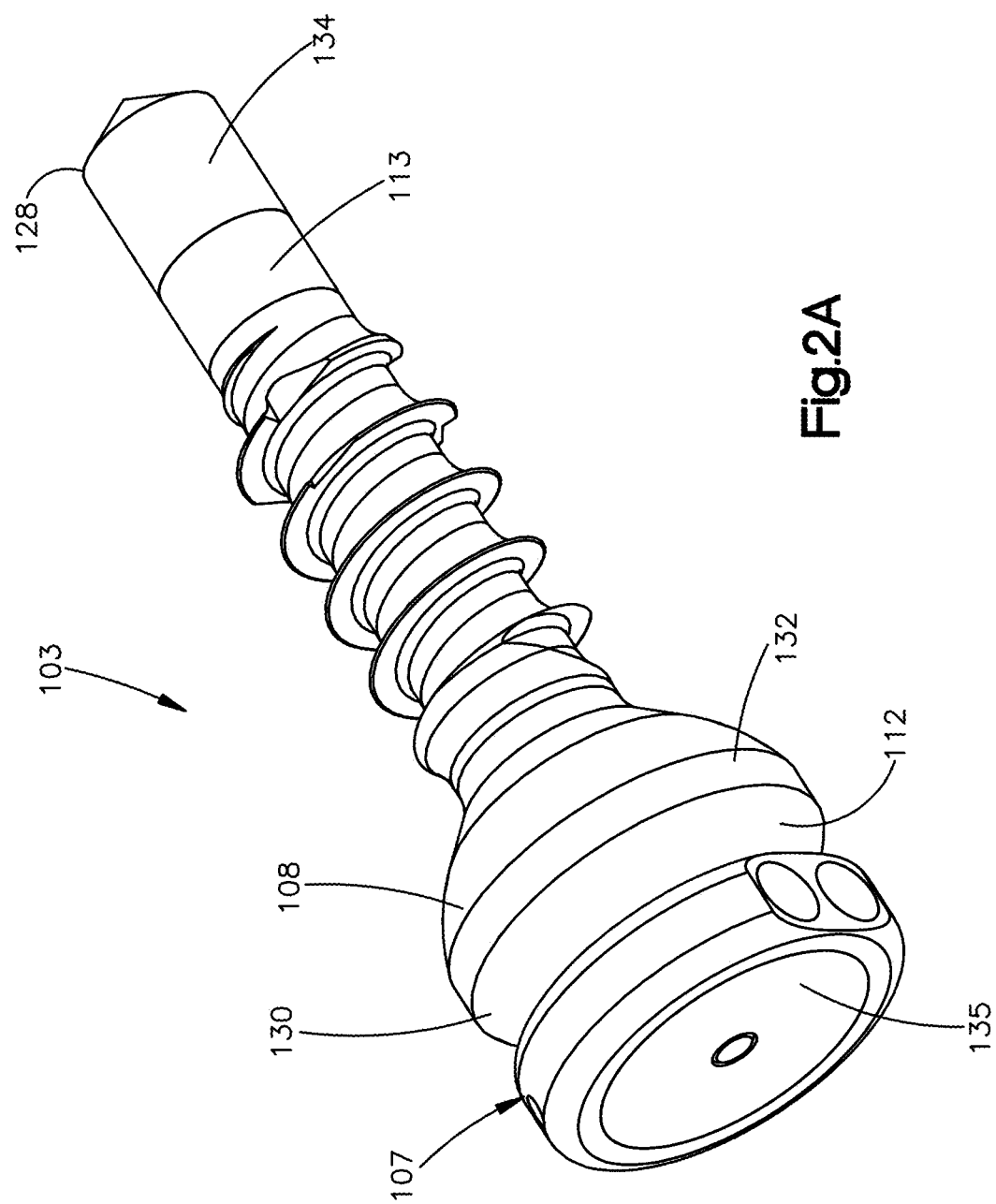
FIG. 2A is a perspective view of a portion of the electrical stimulation anchor system shown in FIG. 1, wherein the illustrated portion includes an electrical stimulation anchor that includes a bone anchor and a connection unit coupled to the bone anchor.
Figure 2B:
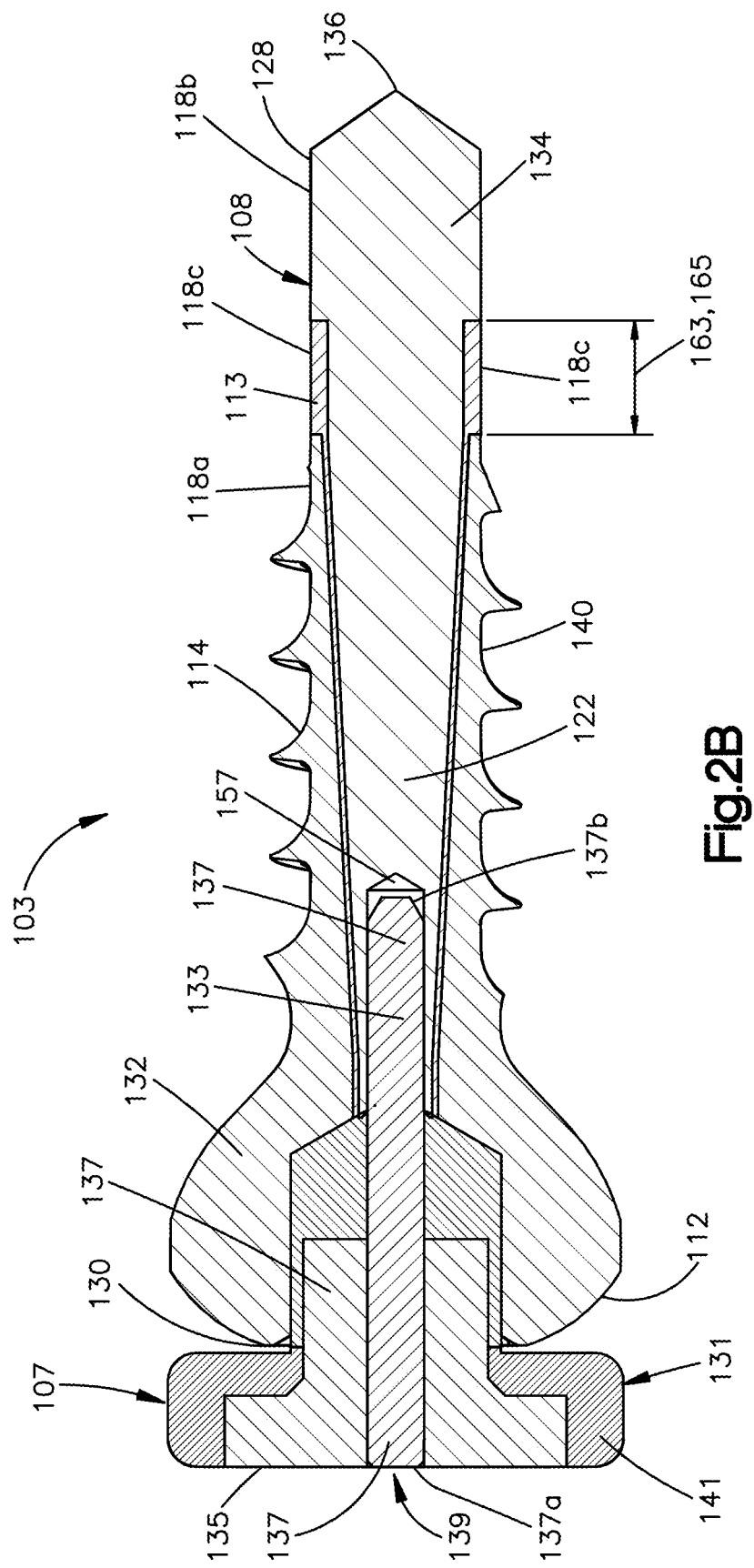
FIG. 2B is a cross section of the electrical stimulation anchor depicted in FIG. 2A.
Figure 4:
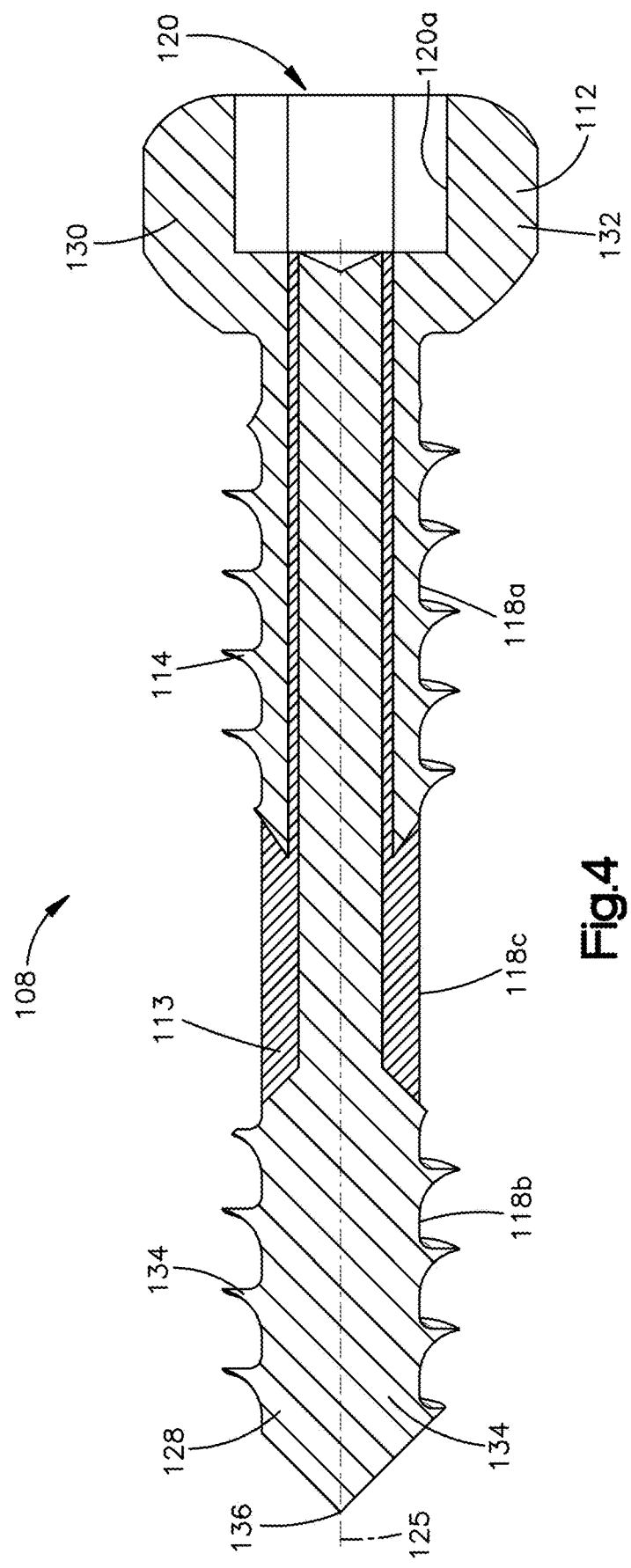
FIG. 4 is another cross section of the bone anchor shown in FIGS. 2A-D, in accordance with another embodiment.
Figure 5:
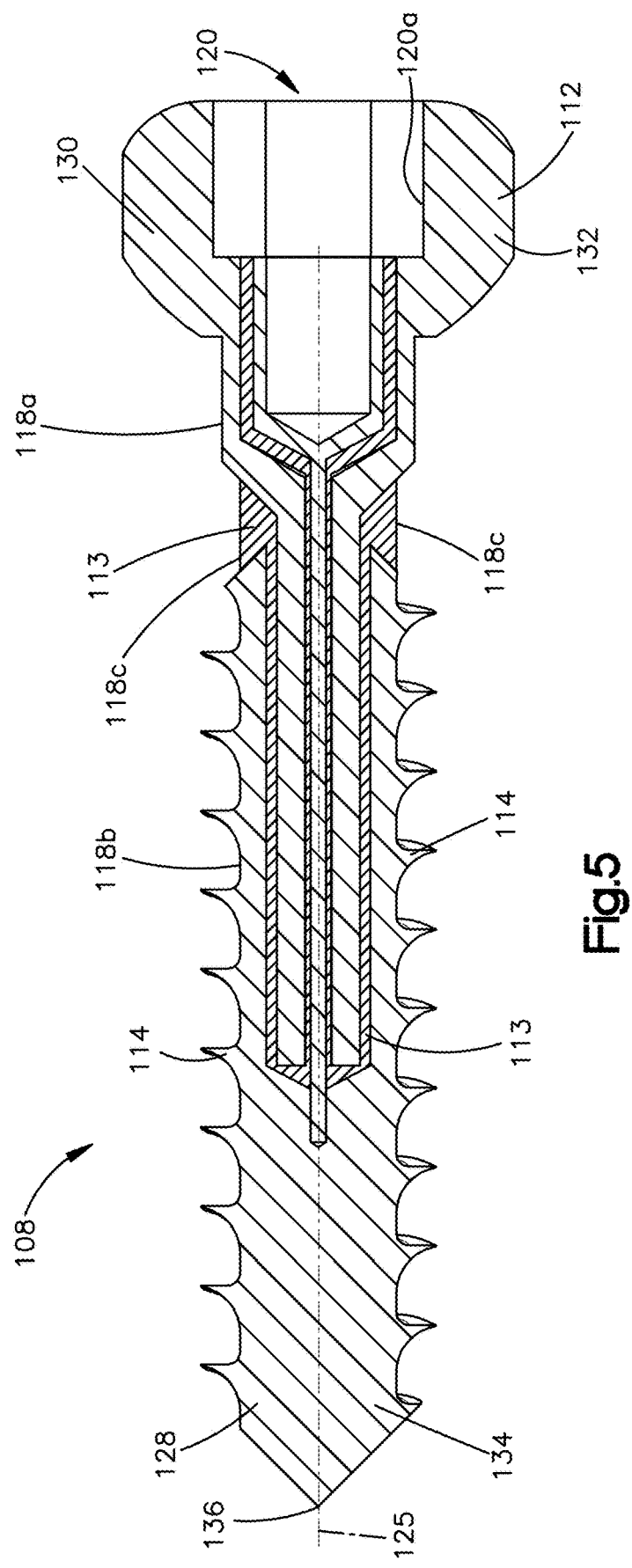
FIG. 5 is yet another cross section of another example bone anchor, in accordance with yet another embodiment.

Referring also to FIGS. 2B and 2C, the bone anchor 108, and thus the electrical stimulation anchor 103, can further include an isolating or insulative portion 113 disposed between the first electrode 132 and the second electrode 134, so as to electrically isolate the first electrode 132 from the second electrode 134 relative to the bone anchor 108. The isolating portion 113 can be composed of any bio-compatible, non-conductive material, such as polymers based materials like poly-ether-ether-ketone (PEEK), or PEKK as desired. The material can also be a bio-resorbable material in certain examples. The isolating portion 113 of the bone anchor 108 can be sized such that when torque is applied to the head 112, the torque is transferred to the tip 136. The bone anchor 108 can define a first electrically conductive outer surface 118a and a second electrically conductive outer surface 118b spaced from the first electrically conductive outer surface 118a along the central anchor axis 125. The insulative portion 113 can define a non-conductive outer surface 118c of the bone anchor 108, such that the first electrically conductive outer surface 118a can be separated from the second electrically conductive outer surface 118b a distance 163 along the central anchor axis 125 substantially equal to a length 165 of the non-conductive outer surface 118c measured along the central anchor axis 125. Referring to FIGS. 3B and 4, in some examples, the shaft 114 and the head 112 can define the first electrically conductive outer surface 118a, and the tip 136 can define the second electrically conductive outer surface 118b, such that the non-conductive outer surface 118c of the isolating portion 113 is disposed at the distal end 128. In an alternative example, with reference to FIG. 5, the head 112 can define the first electrically conductive outer surface 118a, and the shaft 114 and the tip 136 can define the second electrically conductive outer surface 118b, such that the non-conductive outer surface 118c of the isolating portion 113 is disposed at the proximal end 130. Further, at least one, for instance both, of the head 112 and the shaft 114 can define the first electrode 132, and at least one, for instance both, of the shaft 114 and tip 136, can define the second electrode 134. In an example, shaft 114, for instance only the shaft, includes the first electrode 132 and the second electrode 134. The first electrically conductive outer surface 118a can define the first electrode 132, and the second electrically conductive outer surface 118b can define the second electrode 134.

Referring in particular to FIGS. 2A-3C, the bone anchor 108, and in particular the head 112 of the bone anchor 108, can define a recess 120 sized to receive a drill bit or the connection unit 107. In an example, the recess 120 defines a hexagonal shape, although it will be understood that the recess 120 can be alternatively shaped as desired. An inner surface 120a of the head 112 can define the recess 120. In an example, the connection unit 107 defines the connection unit insulator 135 that is configured to isolate the first electrode 132 with respect to the second electrode 134 when the transducer 105 is electrically connected to the first and second electrodes 132 and 134 so as to establish a voltage differential between the first and second electrodes 132 and 134. Referring in particular to FIG. 2C, the connection unit 107 can include a first contact member 131, a second contact member 133, and the connection unit insulator 135 that abuts the first contact member 131 and the second contact member 133 so as to electrically isolate the first contact member 131 and the second contact member 133 from each other. The first contact member 131 can be configured to electrically connect to the first contact of the transducer having the first polarity, and the second contact member 133 can be configured to electrically connect to the second contact of the transducer having the second polarity that is opposite the first polarity.

The connection unit insulator 135 can be disposed between the first contact member 131 and the second contact member 133 so as to prevent the first and second member from contacting each other. The first contact member 131 and the second contact member 133 can be configured to draw current from the transducer 105 so as to have opposite polarities as each other. The first and second contact members 131 and 133 can be composed of electrically conductive material, for instance titanium, stainless steel, or alloys thereof, so as to transfer electrical current. The bone anchor 138 can define a conductive member 122 that defines the tip 136 and the second electrode 134. The conductive member 122 can be composed of electrically conductive material, for instance titanium, stainless steel, or alloys thereof, so as to transfer electrical current. The second contact member 133 can include a pin 137 having a first end 137a and a second end 137b opposite the first end 137a along the central anchor axis 125. The second contact member 133, and thus the pin 137, can be composed of electrically conductive material, for instance titanium, stainless steel, or alloys thereof, so as to transfer electrical current. The pin 137, for instance the second end 137b of the pin 137, can abut the conductive member 122 so as to transfer current to the conductive member 122, and in particular the second electrode 134. The pin 137, for instance the first end 137a of the pin 137, can be configured to electrically couple to the wire 109, in particular an electrical conductor of the wire 109, so as draw current from the transducer 105 and transfer current from the transducer 105 to the second electrode 134. Alternatively, the wire 109 can be configured to be attached directly to the conductive member 122.

Referring in particular to FIGS. 2A-2D, the connection unit insulator 135 can define a connection unit insulator hole 139 sized to receive the pin 137. The pin 137 can be disposed within the connection unit insulator hole 139, such that the pin 137 can be electrically isolated from the first contact member 131 of the connection unit 107. Alternatively, the wire 109 can be received in the connection unit insulator hole 139, such that the electrical conductor of the wire 109 can be electrically isolated from first contact member of the connection unit 107. The first contact member 131 can define a first contact member body 141 and a first contact member shroud 143 extending from the first contact member body 141 toward the distal end 128 of the bone anchor 108. The first contact member shroud 143 can define a shroud outer surface 143a and a shroud inner surface 143b opposite the shroud outer surface 143a. The shroud outer surface 143a can abut the inner surface 120a that defines the recess 120, such that an electrical connection is established between the inner surface 120a and the shroud outer surface 143a, and thus between first contact member 131 and the head 112. The connection unit insulator 135 can define a connection unit insulator body 145 and an insulative or insulating arm 147 that extends from the connection unit insulator body 145 toward the distal end 128 of the bone anchor 108. The insulating arm 147 can define an outer surface 147a that can abut, or be disposed adjacent to so as to face, the shroud inner surface 143b of the shroud 143. The connection unit insulator hole 139 can be centered about the central anchor axis 125. The connection unit insulator body 145 and the insulating arm 147 can define the connection unit insulator hole 139, such that the connection unit insulator hole 139 can extend through opposed surfaces of the connection unit insulator 135 along the central anchor axis 125. The shroud 143 can be sized so as to receive the insulating arm 147. Thus, the insulating arm 147 can be disposed within the shroud 143. Further, the first contact member body 141 can define a recess 151 that can be sized to receive the connection unit insulator body 145. Thus, the connection unit insulator body 145, and thus the connection unit insulator 135, can be disposed within the recess 151 and can be supported by the body 141 of the first contact member 131. The first contact member body 141 can further define at least one, for instance two or more, connection holes 153 configured to establish an electrical connection with the wire 109, in particular at least one electrical conductor of the wire 109.

Referring now again to FIGS. 3A-C, the proximal end 130 and the distal end 128 can each define a respective terminal end of the bone anchor 108. The bone anchor 108 can define a length from its proximal end 130 to its distal end 128 along the central anchor axis 125. It will be understood that the length of the bone anchor 108, and the electrical stimulation anchor 103, can vary as desired.

The electrical stimulation anchor 103, and thus the bone anchor 108, can be elongate from the proximal end 130 to the distal end 128. For instance, the bone anchor 108 can be substantially elongate along the central anchor axis 125 that extends from the proximal end 130 to the distal end 128. The term "substantially" as used herein takes into account manufacturing tolerances and movement that does not alter the nature of fixation to the underlying anatomical structure. It will be appreciated that the central anchor axis 125 of the bone anchor 108 can be straight or curved. Thus, the shaft 114 can be straight or curved as it extends along the central anchor axis 125 from the head 112 to the tip 136.

Figure 2D:
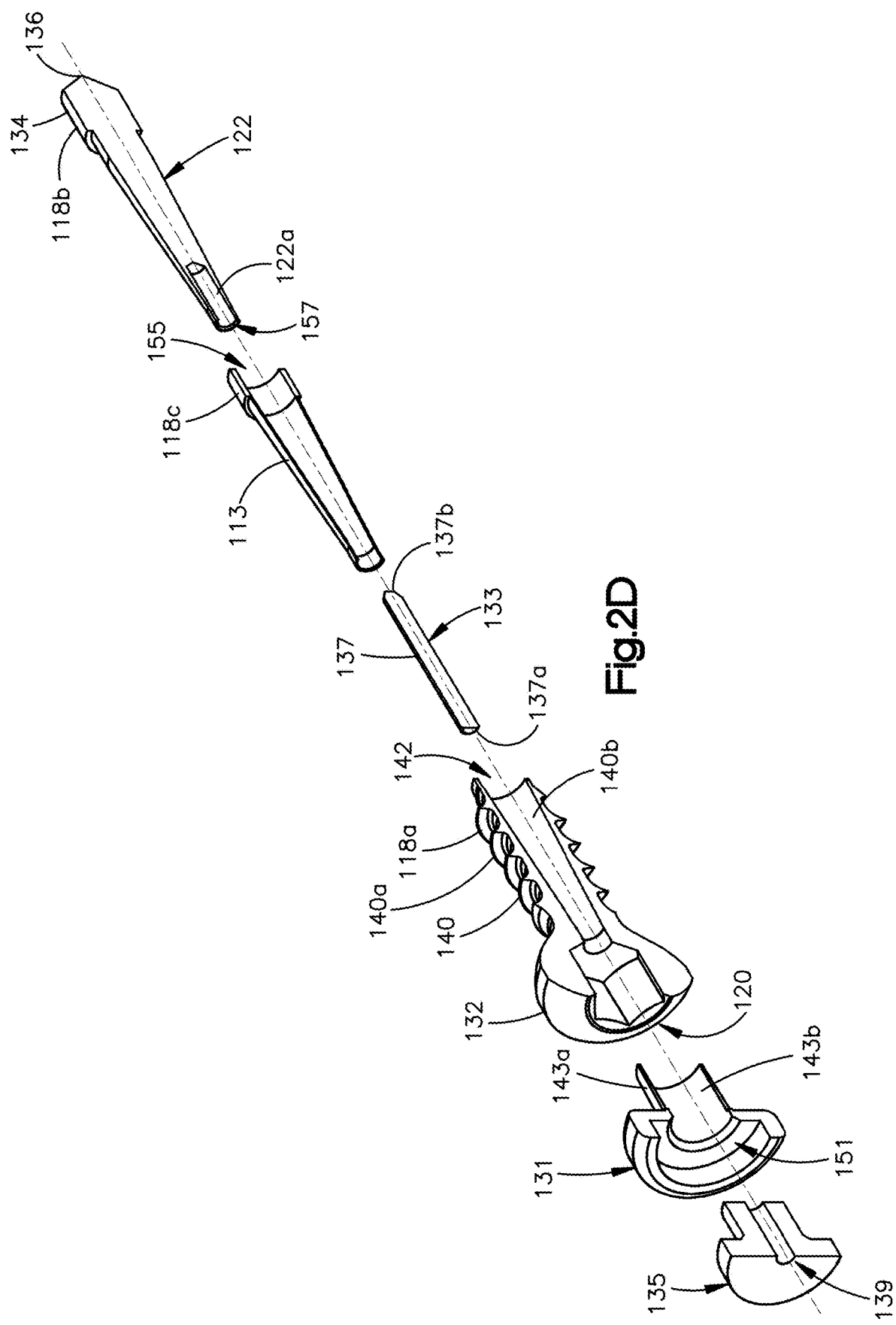
FIG. 2D is a cross section of the exploded view of the electrical stimulation anchor shown in FIG. 2C.

The shaft 114 can include a shaft body 140. At least a portion of each of the second contact member 133, the insulative portion 113, and the conductive member 122 can be disposed within the shaft body 140. Referring in particular to FIG. 2D, the shaft body 140 can include an outer surface 140a and an inner surface 140b opposite the outer surface 140a. For example, the shaft body 140 can define a cavity 142 within which a portion of each of the second contact member 133, the insulative portion 113, and the conductive member 122 can be disposed. The shaft body 140 can define the cavity 142 such that no electrical coil is within the cavity 142, and thus no electrical coil is within the bone anchor 108. Further, the insulative portion 113 can define an insulative cavity 155 within which a portion of each of the second contact member 133 and the conductive member 122 can be disposed. The conductive member 122 can define a connection cavity 157 within which a portion of the second contact member 133 can be disposed. The conductive member 122 can define an inner surface 122a that can define the connection cavity 157. In particular, the second end 137b of the pin can be disposed within the connection cavity 157, so as to contact the inner surface 122a of the connection cavity, thereby establishing an electrical connection between the pin 137 and the conduction member 122, and thus the second electrode 134.

Referring now to FIG. 3C, the isolating portion 113 can taper toward the central anchor axis 125 from the distal end 128 to the proximate end 130, so as to define a cone. Alternatively, referring to FIG. 4, the isolating portion can be centered about the central anchor axis 125 so as to define a cylinder. The cylinder can define a protrusion that extends away from the central anchor axis, so as to define the non-conductive outer surface 118c. It will be understood that the isolating portion 113 can be shaped as desired so as to electrically separate the first electrode 132 from the second electrode 134. Further, the insulative portion 113 can be shaped as desired to electrically separate the first contact member 131 from the second contact member 133, and to define the non-conductive outer surface 118c of the bone anchor 108. For example, referring to FIG. 5, the isolating portion 113 can define two insulative members that mirror each other, and that are disposed on opposite sides of the central anchor axis 125.

Referring now to FIGS. 6-7C, the transducer 105 can include an electrical coil 146 arranged, for instance wound, about a ferromagnetic core 148. The coil 146 can include at least one electrically conductive wire that can be wound around the ferromagnetic core 148. The ferromagnetic core 148 can define an enclosure 150, such that the coil 146 and the core 148 are disposed within the enclosure 150. The enclosure 150 can define an electrical insulator 152 and an outer conductive layer 150a that surrounds the electrical insulator 152. The outer conductive layer 150a can be composed of electrically conductive material, for instance titanium, stainless steel, or alloys thereof. The electrical coil 146 can be disposed within the electrical insulator 152. The electrical insulator 152 can be composed of an injected molded polymer in certain examples. The transducer 105 can further define at least one, for instance first and second contact wires 170a and 170b that are electrically connected to the coil 146 and the wire 109, so as to establish an electrical connection between coil 146 and the wire 109. The first and second contact wires 170a and 170b can be surrounded by first and second contact wire insulators 172a and 172b, respectively.

The transducer 105 can be configured to electrically couple to the first electrode 132 and the second electrode 134. The transducer can be configured to be implanted in soft tissue adjacent to the bone. The transducer 105 can be configured to be oriented in a first orientation that is offset relative to a second orientation defined by the bone anchor. For example, the transducer 105 can be elongate along a direction that is angularly offset with respect to the central anchor axis 125. By way of further example, the transducer 105, and thus the coil 146, can be oriented substantially perpendicular to the bone anchor. In an example, the transducer is configured to be oriented substantially in line with a magnetic field generated by an external coil. The transducer 105 can have an electrical coil positioned in an orientation that is independent from an orientation of the bone anchor 108.

It will be understood that such orientations may allow the transducer 105 to induce a stronger and more consistent electrical current as compared to an orientation that is aligned with the orientation of the bone anchor 108. Further, it will be understood that the embodiments described herein enable the transducer 105 to be positioned in an optimal alignment for power generation, and the bone anchor can be positioned independently from the transducer 105, such that the bone anchor can be positioned for optimal therapeutic effect. Thus, the transducer can be positioned to optimize power generation without inhibiting the positioning of the bone anchor.

In operation, the electrical stimulation anchor system 100, and in particular the transducer 105, can be exposed to a magnetic field that is generated by the PEMF device 102, so as to generate an electric potential between the first and second electrodes. In particular, the magnetic field can be a dynamic field that induces an electric current in the electrical coil 146 of the transducer 105. The current can be transferred to the first and second contact wires 170a and 170b. Thus, the PEMF device 102 can include one or more primary coils, and the coil 146 can include one or more secondary coils. The first and second contact wire 170a and 170 can be connected to opposite ends of the coil 146. In an example, the first and second contact wires 170a and 170b can be connected to coils 146 that are wound in opposite directions as each other. Thus, the first contact wire 170a can have a polarity that is opposite the polarity of the second contact wire 170b. The first and second contact wires can transfer current to first and second conductors of the wire 109, which can transfer current to the first and second contact members 131 and 133, respectively. The first and second contact members 131 and 133 can transfer electrical current to the first and second electrodes 132 and 134, respectively. Thus, for example, the electrical stimulation anchor can be configured to respond to a magnetic field so as to generate an electrical potential between the first electrode 132 and the second electrode 134.

Without being bound by theory, it is recognized herein that this arrangement in which the electrical coil 146 is external to the bone anchor 108 can allow the bone anchor 108 to define a shorter length as compared to other electrical stimulation screws that include the coil. Because the connection unit can electrically connect to an external power source having opposed polarities, the bone anchor can be electrically stimulated without an internal coil that has fixed minimum dimensions for operation. In some examples, this arrangement can allow the bone anchor 108, in particular the shaft 114, to define a smaller circumference as compared to other electrical stimulation screws. For example, the first electrically conductive outer surface 118a and the second electrically conductive outer surface 118b can each define a diameter that is no more than about 5 millimeters (mm). Similarly, in an example, the non-conductive outer surface 118c defines a diameter that is no more than about 5 millimeters. Thus, the shaft 114 can define a diameter that is less than 5 mm. Further, this arrangement can allow the bone anchor 108 to maintain its mechanical strength, such that torque is transferred from the head 112 to the tip 136. Further still, this arrangement can allow the transducer 105, and thus the coil 146, to define a different orientation as compared to the orientation of the bone anchor 108, as desired. Additionally, multiple bone anchors can have different orientations with respect to each other and can be stimulated by the same magnetic field, without sacrificing the consistency of the electrical field that each of the bone anchors generate.

It is further recognized herein that by reducing the length and core diameter of bone anchors in accordance with embodiments described herein, the positioning of the bone anchor can be varied so as to expand the range of therapeutic applications in which the bone anchor can be implemented. The positioning or orientation of the bone anchor can also be varied as desired so as increase the effectiveness of therapeutic applications.

Thus, as described above, a method for treating a fracture or infection in a bone can include inserting an electrical stimulation anchor in the bone such that the fracture or infection is disposed adjacent to first and second electrodes of the electrical stimulation anchor. The first and second electrodes can be electrically connected to a transducer that is external to the electrical stimulation anchor. The transducer can be positioned proximate to the bone, and an electric field can be caused to be generated between the first and second electrodes. Causing the electric field to be generated can include exposing the transducer to a magnetic field so as to generate an electrical current between the transducer and the first and second electrodes. Positioning the transducer proximate to the bone can include placing the transducer in soft tissue adjacent to the bone.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed:

1. An electrical stimulation anchor configured to be electrically coupled to a power source, the electrical stimulation anchor comprising:
    a bone anchor configured to be secured to a bone, the bone anchor defining a head, a tip, and a shaft that connects the head to the tip such that the bone anchor is elongate from the head to the tip along a central anchor axis, the bone anchor further defining a first electrode, a second electrode, and an isolating portion between the first electrode and the second electrode; and
    a connection unit attached to the bone anchor, the connection unit defining a first contact member that electrically connects to the first electrode, a second contact member that electrically connects to the second electrode, and a connection unit insulator that electrically isolates the first contact member with respect to the second contact member, wherein the first and second contact members are configured to draw electrical current from the power source to establish a voltage differential between the first and second electrodes,
    wherein the connection unit is further configured to electrically connect to a first contact of the power source having a first polarity, and a second contact of the power source having a second polarity opposite the first polarity, and
    wherein each of the first and second contact members extend from a location external to the head into the head of the bone anchor.

2. The electrical stimulation anchor as recited claim 1, wherein the connection unit insulator is disposed between the first contact member and second contact member so as to prevent the first and second contact members from contacting each other.

3. The electrical stimulation anchor as recited in claim 2, wherein the bone anchor further defines a first electrically conductive outer surface and a second electrically conductive outer surface spaced from the first electrically conductive outer surface along the central anchor axis.

4. The electrical stimulation anchor as recited in claim 3, wherein each of the first electrically conductive outer surface and the second electrically conductive outer surface define a diameter that is no more than about 5 millimeters.

5. The electrical stimulation anchor as recited in claim 3, wherein the isolating portion defines a non-conductive outer surface of the bone anchor, such that the first electrically conductive outer surface is separated from the second electrically conductive outer surface a distance along the central anchor axis substantially equal to a length of the non-conductive outer surface measured along the central anchor axis.

6. The electrical stimulation anchor as recited in claim 1, wherein the shaft comprises a shaft body that defines a cavity, and at least a portion of the second contact member is disposed within the cavity of the shaft body.

7. The electrical stimulation anchor as recited in claim 6, wherein the shaft body defines the cavity such that no electrical coil is within the bone anchor.

8. The electrical stimulation anchor as recited in claim 7, wherein at least a portion of the isolating portion is disposed within the cavity of the shaft body.

9. The electrical stimulation anchor as recited in claim 8, wherein the isolating portion defines an insulating cavity, and at least a portion of the second contact member is disposed within the insulating cavity.

10. The electrical stimulation anchor as recited in claim 9, wherein the head includes a recess, and the first contact member defines a first contact member body and a first contact member shroud that extends from the first contact member body so as to be disposed within the recess.

11. The electrical stimulation anchor as recited in claim 10, wherein the connection unit insulator defines a connection unit insulator body and an insulating arm supported by the first contact member body of the first contact member.

12. The electrical stimulation anchor as recited in claim 11, wherein the connection unit insulator defines a connection unit insulator hole sized to receive the second contact member.

13. The electrical stimulation anchor as recited in claim 12, wherein the second contact member is disposed within the connection unit insulator hole, such that the second contact member is electrically isolated from the first contact member of the connection unit.

14. The electrical stimulation anchor as recited in claim 13, wherein:
    the second contact member defines a first end and a second end opposite the first end such that the second contact member is elongate from the first end to the second end, the first end of the second contact member is disposed within the hole of the connection unit insulator, and
    the second end of the second contact member is disposed within the cavity of the shaft body.

15. The electrical stimulation anchor as recited claim 1, wherein the power source comprises a transducer having an electrical coil configured to be positioned in an orientation that is independent from an orientation of the bone anchor.

16. An electrical stimulation system comprising:
    a poer source, and
    a first electrical stimulation anchor coupled to the power source, the first electrical stimulation anchor comprising:
        a bone anchor configured to be secured to a bone, the bone anchor defining a head, a tip, and a shaft that connects the head to the tip such that the bone anchor is elongate from the head to the tip along a central anchor axis, the bone anchor further defining a first electrode, a second electrode, and an isolating portion between the first electrode and the second electrode, and
        a connection unit attached to the bone anchor, the connection unit defining a first contact member that electrically connects to the first electrode, a second contact member that electrically connects to the second electrode, and a connection unit insulator that electrically isolates the first contact member with respect to the second contact member, wherein the first and second contact members are configured to draw electrical current from the power source to establish a voltage differential between the first and second electrodes, wherein the connection unit is further configured to electrically connect to a first contact of the power source having a first polarity, and a second contact of the power source having a second polarity opposite the first polarity, and wherein each of the first and second contact members extend from a location external to the head into the head of the bone anchor;

wherein the power source is electrically coupled to the first and second contact members;

wherein the power source is external of the first electrical stimulation anchor.

17. The electrical stimulation system of claim 16, further comprising a second electrical stimulation anchor identical to the first electrical stimulation anchor;

wherein the power source is external to the first electrical stimulation anchor and to the second electrical stimulation anchor; and wherein the power source is electrically coupled to the first electrical stimulation anchor and to the second electrical stimulation anchor.

\* \* \* \* \*